United States Patent
Moussy et al.

(10) Patent No.: US 8,227,470 B2
(45) Date of Patent: Jul. 24, 2012

(54) COMBINATION TREATMENT OF SOLID CANCERS WITH ANTIMETABOLITES AND TYROSINE KINASE INHIBITORS

(75) Inventors: Alain Moussy, Paris (FR); Jean-Pierre Kinet, Lexington, MA (US)

(73) Assignee: AB Science, Paris (FR)

( * ) Notice: Subject to any disclaimer, the term of this patent is extended or adjusted under 35 U.S.C. 154(b) by 210 days.

(21) Appl. No.: 12/522,604

(22) PCT Filed: Jan. 11, 2008

(86) PCT No.: PCT/EP2008/050300
§ 371 (c)(1),
(2), (4) Date: Jul. 9, 2009

(87) PCT Pub. No.: WO2008/084103
PCT Pub. Date: Jul. 17, 2008

(65) Prior Publication Data
US 2010/0093750 A1 Apr. 15, 2010

Related U.S. Application Data (60) Provisional application No. 60/884,743, filed on Jan. 12, 2007.

(51) Int. Cl.
*A61K 31/497* (2006.01)
*A61K 31/33* (2006.01)
*A01N 43/00* (2006.01)
*C07D 277/60* (2006.01)
*C07D 417/00* (2006.01)
*C07D 513/00* (2006.01)
*C07D 275/04* (2006.01)
*C07D 275/06* (2006.01)

(52) U.S. Cl. ............... 514/253.1; 514/183; 548/148; 548/207

(58) Field of Classification Search .............. 514/183, 514/253.1; 548/148, 207
See application file for complete search history.

(56) References Cited

FOREIGN PATENT DOCUMENTS

| WO | WO 2004/001059 A2 | 12/2003 |
|---|---|---|
| WO | WO 2004/014903 A1 | 2/2004 |
| WO | WO 2004/032882 A2 | 4/2004 |
| WO | WO 2005/040139 A2 | 5/2005 |
| WO | WO 2007/026251 A2 | 3/2007 |

OTHER PUBLICATIONS

Yasuda et al. Mol. Cancer 2006, vol. 5, No. 46, pp. 1-10.*
International Search Report issued in application No. PCT/EP2008/050300 on Apr. 28, 2008.
Kleepies et al., "Tyrosine kinase inhibitors and gemcitabine: New treatment options in pancreatic cancer," Drug Resistance Updates, vol. 9, pp. 1-18, 2006.
Georgoulias et al., "Irinotecan plus gemcitabine vs. irinotecan for the second-line treatment of patients with advanced non-small-cell lung cancer pretreated with docetaxel and cesplatin: a multicentre, randomized phase II study," British Journal of Cancer, vol. 91, pp. 482-488, 2004.
Fayette et al.., "News of the year 2005 in sarcomas," Bull. Cancer, vol. 93, No. 1, pp. 83-89, 2006.
Giroux et al., "p8 is a New Target of Gemcitabine in Pancreatic Cancer Cells," Clin. Cancer Res., vol. 12, No. 1, pp. 235-241, 2006.
Duxbury et al., "Focal adhesion kinase gene silencing promotes anoikis and suppresses metastasis of human pancreatic adenocarcinoma cells," Surgery, vol. 135, pp. 555-562, 2004.
Duxbury et al., "RNA interference targeting focal adhesion kinase enhances pancreatic adenocarcinoma gemcitabine chemosensitivity," Biochemical and Biophysical Research Communicatins, vol. 311, pp. 786-792, 2003.
Actualites Pharmaceutiques, "Anti-Cancer Chemotherapy," pp. 36-38 and 41-43, 1992.

* cited by examiner

*Primary Examiner* — Samira Jean-Louis
(74) *Attorney, Agent, or Firm* — Foley & Lardner LLP (57) ABSTRACT

The present invention relates to a method for treating solid cancers including non-small 5 cell lung cancer, pancreatic, bladder, breast and ovarian cancer as well as advanced biliary tract cancers comprising administering at least one antineoplasticagent such as a nucleotide analog, for example gemcitabine, or an antimitotic such as docetaxel, in combination with a tyrosine kinase inhibitor selected from 2-aminoarylthiazoles and 2-aminoaryloxazoles.

17 Claims, 4 Drawing Sheets

COMBINATION TREATMENT OF SOLID CANCERS WITH ANTIMETABOLITES AND TYROSINE KINASE INHIBITORS

The present invention relates to a method for treating solid cancers including non-small cell lung cancer, pancreatic, bladder, breast and ovarian cancer, prostate cancer, as well as advanced biliary tract cancers comprising administering at least one antineoplastic agent such as a nucleotide analog, for example gemcitabine, or an antimitotic such as docetaxel, in combination with a tyrosine kinase inhibitor selected from 2-aminoarylthiazoles and 2-aminoaryloxazoles.

BACKGROUND OF THE INVENTION

Pancreatic cancer is the fourth to fifth leading cause of cancer-related death in the Western world. The prognosis for diagnosed patients is poor with an overall 5-years survival rate less than 5%, 12 month survival rate of 10%, and a median survival time of approximately 3-5 months after tumour detection. Major reasons for this poor outcome are the inability to diagnose pancreatic cancer at an early stage because of the lack of specific symptoms, inaccessible location of the pancreas, and an early occurrence of metastatic disease. To date, current radiation and chemotherapy regimens have not achieved significant improvement in the long term survival of pancreatic cancer patients, emphasising the importance of developing novel combination therapies more effective against advanced stages of this disease.

The causes of pancreatic cancer are not yet well understood but increasing attention has been directed towards the role of growth factors in the pathogenesis of the disease. Numerous growth factors and their receptors are over-expressed during the progression of pancreatic cancer such as EGF, PDGF and VEGF, suggesting the importance in evaluating selective inhibitor of receptor tyrosine kinase in this disease.

Gemcitabine (2',2',-dofluoro-2',-deoxycytidine) is a nucleoside analog of deoxycytidine marketed as GEMZAR™ that interferes with DNA synthesis through inhibition of ribonucleotide reductase and competition with dCTP for incorporation into DNA. It is currently the treatment of reference for several cancers such as pancreatic cancers and it is associated with radiotherapy. However, treatment protocol with gemcitabine alone has little influence on patients' survival.

Thus, as of today, there is no cure for pancreatic cancer.

Much research is being performed to find compounds that would either act in synergy or abolish gemcitabine resistance observed in numerous cancers. Despite numerous efforts, data obtained so far suggested the implication of the Bcl2 gene family in pancreatic cancer resistance to gemcitabine but has not led to significant improvement of treatment protocols. Also, several attempts to find effective combination therapy has been described but are not successful. For example anti-angiogenesis compounds have been co-administered with gemcitabine and no improvement in survival have been observed so far.

AB1010 (Masitinib) is a novel tyrosine kinase inhibitor developed by AB Science part of 2-aminoarylthiazoles derivatives that targets c-Kit and PDGFR13 receptors, and which are the subject matter of WO 2004/014903. AB1010 is currently being evaluated in clinical trials in number of malignancies and so far the results are very encouraging.

The pre-clinical data reported herein clearly show that AB1010 reverse resistance of pancreatic tumour cell lines to the gemcitabine. These results show that AB1010 has great potential as combination therapy in gemcitabine treated patients for several cancers such as non-small cell lung cancer, pancreatic, bladder, breast and ovarian cancer as well as advanced biliary tract cancers. We also found that AB1010 sensitize the action of antimitotics such as docetaxel. Although the exact mechanism of action of 2-aminoarylthiazoles which are C-KIT/PDGF-R inhibitors as defined here below is not yet fully elucidated, we discovered that theses tyrosine kinase inhibitors are able to block the FAK pathway in the context of cancer cells resisting to conventional gemcitabine or docetaxel treatment. Blocking the FAK pathway might explain the sensitization of chemotherapeutic agents as tumor cells loss their adherence properties impeding cells migration. In any case, this discovery also imply that cancer cells treated with the above compounds are less prone to metastasis.

Thus, we provide here for the first time a combined treatment of solid cancers with at least one antimetabolite, such as gemcitabine or docetaxel, and a tyrosine kinase inhibitor selected from 2-aminoarylthiazole and 2-aminoaryloxazole allowing to reverse resistance as well as sensitize cancer cells to standard chemotherapy.

DESCRIPTION

The present invention generally relates to the field of solid cancer treatment. It provides a new method for treating solid cancers comprising administering a 2-aminoarylthiazole or 2-aminoaryloxazole (WO 2004/014903 and WO 2005/040139 respectively and incorporated herein by reference) and at least one antineoplastic agent, more particularly at least one antineoplastic agent selected from antimetabolites, such as a nucleotide analog and/or an antimitotic agent, in patients in need of such treatment.

Among solid cancers, the invention is more specifically directed to the treatment of non-small cell lung cancer, pancreatic cancer, bladder, breast and ovarian cancer, prostate cancer, oesophageal cancer, as well as advanced biliary tract cancers.

By <<antineoplastic agent>>, it is referred herein to marketed medicament for the treatment of cancers, for example the compounds as depicted in Actuanté Pharmaceutiques n°302 (October 1992) pages 38 to 39 et 41 to 43 incorporated by reference. More specifically, it will be referred to antimetabolites selected from antimitotics which are compounds known in the art to inhibit mitosis for example by inhibiting tubuline depolymerization. These antimetabolites include docetaxel, paclitaxel, vinblastine, vinorelbine and etoposide.

For example, docetaxel (CAS number 114977-28-5, Taxotere™) as shown below is effective against numerous tumors and especially metastatic breast cancer, lung and prostate cancers:

Other antimetabolites are nucleotide analogs including but are not limited to:

purine analogs such as thio-6-guanine, pentostatine, pyrimidine analogs such as cytosine arabino side, fluoro-5-uracile (5FU), fluorouridine-desoxyribose, capecitabine or gemcitabine, as well as adenine analogs such as fludarabine. As defined herein antimetabolites do not encompass 2-Chloro-2'-desoxyadenosine (2-CDA), Cladribine, Merck Index (12th ed.) # 2397.

For example, the antimetabolite is gemcitabine CAS number 95058-81-4 (4-amino-1-[3,3-difluoro-4-hydroxy-5-(hydroxymethyl) tetrahydrofuran-2-yl]-1H-pyrimidin-2-one):

Gemcitabine replaces cytidine during DNA replication resulting in apoptosis in cancer cells. It is used in various carcinomas: non-small cell lung cancer, pancreatic cancer, and breast cancer and is being investigated for use in oesophageal cancer.

In a first embodiment preferred, 2-aminoarylthiazole or 2-aminoaryloxazole (hereafter referred as AB compounds) as mentioned above are compounds of formula I, which may represent either free base forms of the substances or pharmaceutically acceptable salts thereof:

FORMULA I wherein substituents Z, A, B, B', Q and R1-R6 in Formula I are defined as follows:

Z is oxygen or sulfur.
A and B' is one of the following:
i) (R7)N(CH2)$_n$ where n is 0 or 1
ii) O(CH2)$_n$ where n is 0 or 1
iii) S(CH2)$_n$ where n is 0 or 1
iv) (CH2)$_n$ where n is 0, 1 or 2
v) C(O)(CH2)$_n$ where n is 0 or 1
or when A and B' each are a nitrogen, they may be taken together to form a bivalent radical of formula:

(a)

where s and t each independently is 1 or 2 and X1 being O, S, NR10, N[C(=O)R10] or (CH2)$_n$ where n is 0 or 1, and wherein each hydrogen in said formula (a) may be substituted with halo or $C_{1-4}$alkyl.
B is one of the following:
i) (R7)N
ii) Oxygen
iii) S(O)$_n$ where n is 0, 1 or 2
iv) CH(R7)(R8)
v) C=δ, where δ is oxygen, sulfur, NH or N—CN
vi) C(R7)=C(R8)
vii) N=C(R7)

R7 and R8 each independently are hydrogen, $C_{1-4}$alkyl, $C_{2-6}$alkenyl, $C_{2-6}$alkynyl, $C_{3-7}$cycloalkyl, $C_{1-4}$haloalkyl, $C_{1-4}$alkoxy, $C_{1-4}$hydroxyalkyl, $C_{1-4}$alkylamino.
R1 and R2 is selected from:
i) hydrogen, halogen (selected from F, Cl, Br or I), or
ii) an alkyl$^1$ group defined as a linear, branched or cycloalkyl group containing from 1 to 10 carbon atoms (such as for example from 2 to 4 or 1 to 5 or 1, 2, 3, 4, or 5 carbon atoms) and optionally substituted with one or more hetereoatoms such as halogen (selected from F, Cl, Br or I), oxygen, and nitrogen (the latter optionally in the form of a pendant basic nitrogen functionality); as well as trifluoromethyl, carboxyl, cyano, nitro, formyl; as well as CO—R, COO—R, CONH—R, SO2-R, and SO2NH—R wherein R is a linear or branched alkyl group containing 1 to 10 carbon atoms and optionally substituted with at least one heteroatom, notably a halogen (selected from F, Cl, Br or I), oxygen, and nitrogen, the latter optionally in the form of a pendant basic nitrogen functionality; as well as a cycloalkyl or aryl$^1$ or heteroaryl$^1$ group optionally substituted by a pendant basic nitrogen functionality, or
iii) an aryl$^1$ group defined as phenyl or a substituted variant thereof bearing any combination, at any one ring position, of one or more substituents such as
Halogen (selected from I, F, Cl or Br);
an alkyl$^1$ group;
a cycloalkyl, aryl or heteroaryl group optionally substituted by a pendant basic nitrogen functionality;
trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the form of a basic nitrogen functionality;
NHCO—R or NHCOO—R or NHCONH—R or NHSO2-R or NHSO2NH—R or CO—R or COO—R or CONH—R or SO2-R or SO2NH—R or C(NOH)NH2, C(N)NH2 wherein R corresponds to hydrogen, alkyl$^1$, aryl or heteroaryl, or
iv) a heteroaryl$^1$ group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, benzoxazole, benzothiazole quinolinyl group, which may additionally bear any combination, at any one ring position, of one or more substituents such as halogen (selected from F, Cl, Br or I);
an alkyl$^1$ group;
a cycloalkyl, aryl or heteroaryl group optionally substituted by a pendant basic nitrogen functionality,
trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the form of a basic nitrogen functionality;
NHCO—R or NHCOO—R or NHCONH—R or NHSO2-R or NHSO2NH—R or CO—R or COO—R or CONH—R or SO2-R or SO2NH—R wherein R corresponds to hydrogen, alkyl$^1$, or v) an O-aryl$^1$, or NH-aryl$^1$, or O-heteroaryl$^1$ or NH-heteroaryl$^1$ group vi) trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the form of a basic nitrogen functionality, or vi) NHCO—R or NHCOO—R or NHCONH—R or NHSO2-R or NHSO2NH—R or CO—R or COO—R or CONH—R or SO2-R or SO2NH—R wherein R corresponds to hydrogen, alkyl$^1$, aryl$^1$ or heteroaryl$^1$.

R3, R4, R5 and R6 each independently are selected from hydrogen, halogen (selected from F, Cl, Br or I), a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality; as well as trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONH—R, SO2-R, and SO2NH—R wherein R corresponds to hydrogen, alkyl$^1$, aryl or heteroaryl.

and wherein Q is selected from:
i) Alkyl$^1$
ii) Aryl$^1$
iii) Heteroaryl$^1$
as defined above.

Unless otherwise specified, the below terms used herein are defined as follows:

As used herein, the term an "aryl group" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents.

In one embodiment, the aryl group is a monocyclic ring, wherein the ring comprises 6 carbon atoms, referred to herein as "(C6)aryl."

As used herein, the term "alkyl group" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents.

As used herein, the term "alkoxy" refers to an alkyl group which is attached to another moiety by an oxygen atom. Examples of alkoxy groups include methoxy, isopropoxy, ethoxy, tert-butoxy, and the like. Alkoxy groups may be optionally substituted with one or more substituents.

As used herein, the term "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on a nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

The term "heterocycle," as used herein, refers collectively to heterocycloalkyl groups and heteroaryl groups.

As used herein, the term "heterocycloalkyl" means a monocyclic or polycyclic group having at least one heteroatom selected from O, N or S, and which has 2-11 carbon atoms, which may be saturated or unsaturated, but is not aromatic. Examples of heterocycloalkyl groups including (but not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen (chloro, iodo, bromo, or fluoro); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —$C(O)NR_{11}R_{12}$, —$NR_{13}C(O)R_{14}$, a halo, —$OR_{13}$, cyano, nitro, a haloalkoxy, —$C(O)R_{13}$, —$NR_{11}R_{12}$, —$SR_{13}$, —$C(O)OR_{13}$, —$OC(O)R_{13}$, —$NR_{13}C(O)NR_{11}R_{12}$, —$OC(O)NR_{11}R_{12}$, —$NR_{13}C(O)OR_{14}$, —$S(O)rR_{13}$, —$NR_{13}S(O)rR_{14}$, —$OS(O)rR_{14}$, $S(O)rNR_{11}R_{12}$, —O, —S, and —N—$R_{13}$, wherein r is 1 or 2; $R_{11}$ and $R_{12}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or $R_1$ and $R_{12}$ taken together with the nitrogen to which they are attached is optionally substituted heterocycloalkyl or optionally substituted heteroaryl; and $R_{13}$ and $R_{14}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl.

The term "cycloalkyl" means a saturated cyclic alkyl radical having from 3 to 10 carbon atoms. Representative cycloalkyls include cyclopropyl, 1-methylcyclopropyl, cyclobutyl, cyclopentyl, cyclohexyl, cycloheptyl, cyclooctyl, cyclononyl, and cyclodecyl. Cycloalkyl groups can be optionally substituted with one or more substituents.

The term "halogen" means —F, —Cl, —Br or —I.

Among the particular compounds of formula I, the invention is directed to compounds of the following formula II:

FORMULA II

Z is oxygen or sulfur.

Aryl[1], Heteroaryl[1], R1, R2 and R3 have the meaning described above.

An example of preferred compounds of the above formula is depicted below:

001: N-{3-[5-(4-Cyano-phenyl)-oxazol-2-ylamino]-4-methyl-phenyl}-3-trifluoro methyl-benzamide 002: 4-(4-Methyl-piperazin-1-ylmethyl)-N-[4-methyl-3-(4-pyridin-3-yl-thiazol-2-ylamino)-phenyl]-benzamide (Masitinib-AB1010)

Among the particular compounds of formula I, the invention is directed to compounds of the following formula III:

FORMULA III

Z is oxygen or sulfur.

Aryl[1], Heteroaryl[1], R1, R2 and R3 have the meaning described above.

An example of preferred compounds of the above formula is depicted below:

003: N-(3-Chloro-phenyl)-4-methyl-3-(5-pyridin-4-yl-oxazol-2-ylamino)-benzamide 004: 4-Methyl-N-[4-(4-methyl-piperazin-1-ylmethyl)-phenyl]-3-(4-pyridin-3-yl-thiazol-2-ylamino)-benzamide Among the particular compounds of formula I, the invention is directed to compounds of the following formula IV:

FORMULA IV

Wherein W is C=O or SO2.

Z is oxygen or sulfur.

L is selected from Alkyl', Aryl[1] or Heteroaryl[1] as defined above.

R1, R2, R3, R4, R5 and R6 have the meaning described above.

R9 is selected from hydrogen, a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality; $C_{1-6}$alkyloxy, amino, hydroxyl.

An example of preferred compounds of the above formula is depicted below:

005: N-[4-Methyl-3-(5-pyridin-4-yl-oxazol-2-ylamino)-phenyl]-C-phenyl-methanesulfonamide 006: N-[4-Methyl-3-(4-pyridin-3-yl-thiazol-2-ylamino)-phenyl]-C-phenyl-methane sulfonamide The compounds of the present invention may be prepared using the general protocols described in our previous applications WO 2004/014903 and WO 2005/040139.

In still another embodiment, the invention contemplates the method mentioned above, wherein said AB compound is selected from 2-(3-amino)arylamino-4-aryl-thiazoles such as those for which the applicant filed WO 2004/014903, incorporated herein in the description, especially compounds of formula V:

FORMULA V wherein X is R or NRR' and wherein R and R' are independently chosen from H, an aryl, a heteroaryl, an alkyl, or a cycloalkyl group optionally substituted with at least one heteroatom, such as for example a halogen chosen from F, I, Cl and Br and optionally bearing a pendant basic nitrogen functionality; or an aryl, a heteroaryl, an alkyl or a cycloalkyl group substituted with an aryl, a heteroaryl, an alkyl or a cycloalkyl group optionally substituted with at least one heteroatom, such as for example O, N, a halogen chosen from F, I, Cl and Br or optionally bearing a pendant basic nitrogen functionality,

$R^2$ is hydrogen, halogen or a linear or branched alkyl group containing from 1 to 10 carbon atoms, trifluoromethyl or alkoxy;

$R^3$ is hydrogen, halogen or a linear or branched alkyl group containing from 1 to 10 carbon atoms, trifluoromethyl or alkoxy;

$R^4$ is hydrogen, halogen or a linear or branched alkyl group containing from 1 to 10 carbon atoms, trifluoromethyl or alkoxy;

$R^5$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from O, N, I, Cl, Br and F, and/or bearing a pendant basic nitrogen functionality. Examples of group X include structures a to m shown below, wherein the wavy line or arrow corresponds to the point of attachment to core structure of formula V above:

Among group a to f, is preferentially group d. Also, for g to m, the arrow may include a point of attachment to the core structure via a phenyl group.

In still another embodiment, the invention embraces the method as depicted above wherein said inhibitor is selected from compounds of Formula I, II, III, IV or V.

It also relates to the use of the compounds defined above in combination with at least one antineoplastic agent as defined above for treating solid cancers, including but not limited to non-small cell lung cancer, pancreatic cancer, bladder, breast and ovarian cancer, as well as advanced biliary tract cancers.

The invention also relates to a product or pharmaceutical composition for a simultaneous or sequential administration of an inhibitor selected from compounds of Formula I, II, III, IV or V as defined above and at least one antineoplastic agent as defined above for treating solid cancers, including but not limited to non-small cell lung cancer, pancreatic cancer, bladder, breast and ovarian cancer, oesophageal cancer, as well as advanced biliary tract cancers.

The invention also relates to the use of an inhibitor selected from compounds of Formula I, II, III, IV or V as defined above and at least one antineoplastic agent as defined above for preparing a medicament for a simultaneous, separate or sequential administration for treating solid cancers, including but not limited to non-small cell lung cancer, pancreatic cancer, bladder, breast and ovarian cancer, oesophageal cancer, as well as advanced biliary tract cancers.

The above invention contemplates especially the treatment of patients afflicted with unresectable pancreatic adenocarcinoma, particularly those resistant to gemcitabine alone plus radiotherapy protocols.

More specifically, the compound of formula I is 4-(4-Methyl-piperazin-1-ylmethyl)-N-[4-methyl-3-(4-pyridin-3-yl-thiazol-2-ylamino)-phenyl]-benzamide (Masitinib-AB1010)

In the above depicted embodiment, the combination product can be designed or specified so that a compound of Formula I, II, III, IV or V is administered before at least one said neoplastic agent.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

More particularly, the invention relates to a pharmaceutical composition intended for oral administration. Pharmaceutical compositions suitable for use in the invention include compositions wherein compounds for depleting mast cells, such as c-kit inhibitors, or compounds inhibiting mast cells degranulation are contained in an effective amount to achieve the intended purpose. The determination of an effective dose is well within the capability of those skilled in the art. A therapeutically effective dose refers to that amount of active ingredient, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred.

For example, the above patients can receive a daily or weekly administration of from 40 mg to 800 mg of AB compound of formula I, II, III, IV or V as defined above, for example 40 mg, 100 mg, 200 mg, or even 400 mg or 800 mg depending of the patient's weight. This is followed by administration of at least one antineoplastic compound.

In this regard, gemcitabine can be administered by intravenous infusion at a dose of for example 1000 mg/m2 over 30 minutes once weekly (for up to 7 weeks). Subsequent cycles should consist of infusions once weekly for 3 consecutive weeks out of every 4 weeks.

In addition, the above combined therapy may further include administration of carboplatin for the treatment of patients with advanced ovarian cancer that have relapsed at least 6 months after completion of platinum-based therapy. In Breast Cancer, the above combined therapy may further include administration of paclitaxel. In Non-Small Cell Lung Cancer, cisplatin may further be administrated for the first-line treatment of patients with inoperable, locally advanced (Stage IIIA or IIIB), or metastatic (Stage IV) non-small cell lung cancer.

Alternatively, docetaxel at for example 75 mg/m2/daily can be administered following administration of AB compound of formula I, II, III, IV or V as defined above.

EXAMPLE 1

Activity of AB Compounds

The action of AB compounds in inhibiting c-kit tyrosine kinase activity has been demonstrated in an ELISA assay using the purified intracellular soluble domain (567-976) of c-kit expressed in baculovirus measuring phosphorylation of a peptide target containing a tyrosine group. AB compounds potently inhibited enzymatic activity with an IC50 of below 0.1 µM. The specific anti-proliferative activity of AB compounds was exhibited in a selection of mammalian cell lines suitable for testing the specific activity of c-kit tyrosine kinase inhibitors with juxtamembrane mutations.

AB compounds are potent and selective inhibitors of c-kit and also inhibit PDGF-R in vivo at IC50 below 1 µM.

TABLE I

| Enzyme | IC50 [µM] | Cell line | IC50 [µM] |
| --- | --- | --- | --- |
| c-Kit | below 0.1 | Ba/F3 Kit | 0.1 < IC50 < 1 |
| PDGF-beta | below 1 | Ba/F3 PDGFR | 0.1 < IC50 < 1 |
| FGFR3 | | LP1, NC1, OPM2 | <2 |
| ABL1 | below 10 | Ba/F3 p210Bcr-Abl | IC50 > 1 |
| VEGFR1 | IC50 > 100 | Ba/F3 IL3 | IC50 > 1 |
| EGFR | IC50 > 100 | Ba/F3 EGFR | IC50 > 1 |
| FGFR1 | IC50 > 100 | Ba/F3 RET | IC50 > 1 |
| FLT3 | IC50 > 100 | Ba/F3 TRKB | IC50 > 1 |
| JAK2 | IC50 > 100 | Ba/F3 FGFR1 | IC50 > 1 |
| AKT1 | below 100 | Ba/F3 FGFR3 | IC50 > 1 |
| PKC-alpha | about 100 | Ba/F3 FLT3 WT | IC50 > 1 |
| SRC | IC50 > 100 | Ba/F3 FLT3 ITD | IC50 > 1 |
| IGF1R | IC50 > 100 | Ba/F3 Tel-JaK1 | IC50 > 1 |
| PIM1 | below 50 | Ba/F3 Tel-JaK2 | IC50 > 1 |
| | | Ba/F3 Tel-JaK3 | IC50 > 1 |

AB compounds inhibit the proliferation of cells that express JM mutations of c-kit with an IC50 of less than 0.1 µM. The absence of non-specific cytotoxicity was demonstrated through proliferation of human T-lymphocyte populations, and of the Ba/F3 cell line in the presence of IL-3. The ability of AB compounds to induce apoptosis was demonstrated in a human mast cell line expressing the JMΔ27 mutated c-kit. In this experiment, after 48 hours, 0.1 μM AB1010 induced apoptosis of approximately 50% versus control cells in which 10% of cells were apoptotic. In addition, a separate cell line (Ba/F3-derived) expressing JMΔ27 was tested and apoptosis was induced to a level of approximately 85%.

EXAMPLE 2

Use of AB Compounds for Treating Pancreatic Cancer Combined with Gemcitabine 2.1 Drugs and Chemicals:
2.1.1 MasItinib

| | |
|---|---|
| 1. Name: | AB1010 |
| 2. Molecular formula: | $C_{28}H_{30}N_6OS \cdot CH_4O_3S$ |
| 3. Supplier: | Archemis |
| 4. Batch number: | RAN0328 |
| 5. Description: | received as a white powder |
| 6. Stock solution: | 20 mM in DMSO |
| 7. Storage conditions: | +4° C. as powder protected from light. −80° C. as solution in DMSO |

2.1.2 Cytotoxic Agents:

Gemcitabine (2', 2',-dofluoro-2',-deoxycytidine) was from Eli Lilly and is a nucleoside analogue of deoxycytidine that interferes with DNA synthesis.

The other agents were purchased from Sigma Aldrich Corporation and are poisons of microtubules (Paclitaxel or Taxol and Docetaxel or Taxotere), anti-topoisomerase I (Irinotecan or CPT-11).

2.2 Cell Culture

Pancreatic, colon and prostate cancer cell lines (generous gift from Dr. Juan Iovanna, INSERM U624, Marseille, France), breast and ovarian cancer cell lines (generous gift from Dr. Patrice Dubreuil, UMR 599 INSERM, Marseille, France), and lung cancer cell line (generous gift from Pr. Christian Auclair, UMR 8113 CNRS) were cultured as monolayers in RPMI 1640 medium containing L-glutamine supplemented with 100 U/mL penicillin and 100 μg/mL streptomycin, and 10% v/v heat-inactivated foetal calf serum (AbCys Lot SO2823S1800) under standard culture conditions (5% CO2, 95% air in humidified chamber at 37° C.).

During proliferation assay, all cells were grown in medium containing 1% FCS.

2.3 Experimental Design

Colorimetric cell proliferation and viability assay (reagent WST-1 purchased from Roche cat N° 1644807)

The cells were washed once and resuspended in RPMI 1% FCS. Cells at $1.10^4/50$ μl were plated per well of a 96 well plate.

Drug dilutions were prepared in a 96 well plate and obtained by sequential dilutions of AB1010 or gemcitabine in RPMI 1.

Treatment was started by the addition of 50 μl of a 2× concentrated drug solution to a final volume of 100 μl.

For treatment with combination of AB1010 and gemcitabine, the cells were first resuspended in medium RPMI 1% FCS containing AB1010 at the concentrations of 0, 2, 5 and 10 μM. $1.10^4$ cells/50 μl were plated per well of a 96 wells plate and the plates placed in the incubator o/n before treatment with cytotoxic agents. Cytotoxic agent treatment was initiated by addition of 50 μl of a 2× drug dilution (and containing the respective AB1010 drug concentration) to a final volume of 100 μl. AB1010 final concentrations remained 0, 2, 5 and 10 μM. After incubating for 48-72 hours at 37° C., 10 μl of a ½ dilution of WST-1 reagent was added to each well and the plates were returned to the incubator for an additional 4 hours. The absorbance of the samples was measured at 490 nm using an EL800 Universal microplate reader (Bio-Tek Instruments Inc.).

A background control without cells was used as a blank for the ELISA reader.

The positive control of the assay corresponds to the cell proliferation obtained in the absence of drug treatment (100% proliferation).

Each sample was done in duplicate, the absorbance values were transferred to an excel file, the average and standard deviation of the duplicates were calculated and expressed as a percentage of the proliferation obtained in absence of treatment.

2.3—Results:

In order to assess the benefits of using AB1010 in combination therapy for cancer treatment, we performed preclinical studies involving tumour cell lines. The project consisted in testing the ability of AB1010 to sensitize tumour cell lines to cytotoxic agents using in vitro proliferation assays. We studied at first pancreatic tumour cells lines that exhibit strong resistance to the cytotoxic agent gemcitabine (standard treatment in pancreatic cancer).

3.1 AB1010 Sensitizes Pancreatic Cancer Cell Lines to Gemcitabine

To determine the IC50 concentration of gemcitabine on pancreatic cell lines, the cells were grown in 1% FCS and exposed to different doses of the drug.

Figure 1:
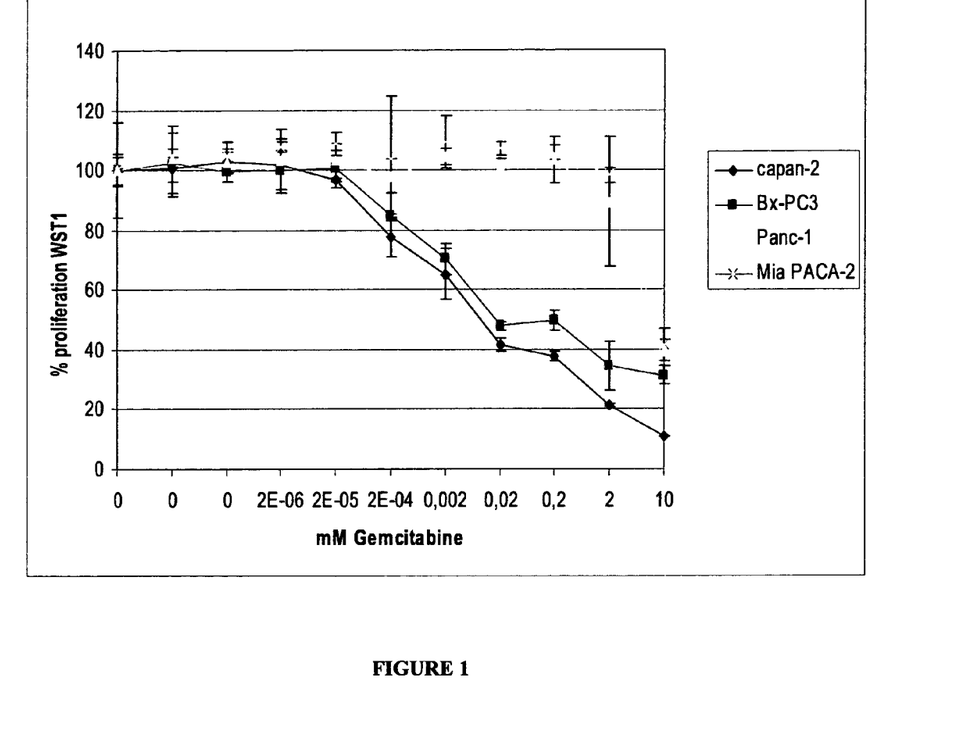
FIG. 1 illustrates relative proliferation of cell lines with gemcitabine and capan-2, Bx-PC3, Panc-1, and Mia PACA-2.

FIG. 1 illustrates the lack of sensitivity to gemcitabine of Mia Paca-2 and Panc-1 (as previously described by Giroux et al. 2006) while the proliferation of Capan-2 and BxPC-3 sensitive cell lines is efficiently inhibited with an IC50=2-20 nM.

To determine the IC50 concentration of gemcitabine used in association with AB1010, pancreatic cell lines grown in 1% FCS were pre-treated with AB1010 for about 12-16 hours before being exposed to different doses of the gemcitabine.

Figure 2A:
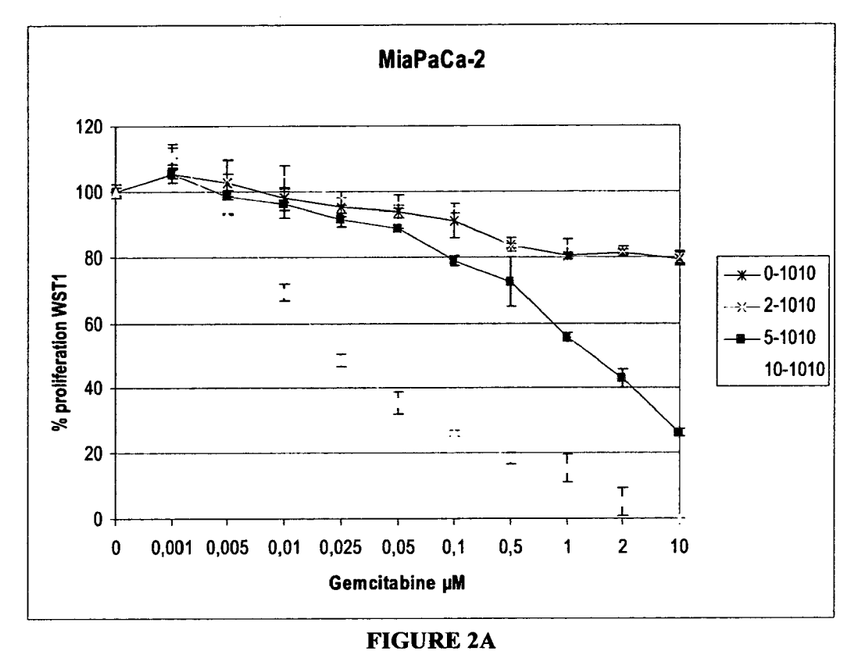
FIGS. 2A and 2B show the effect of AB1010 pretreatment on resistance to gemcitabine of tumor cell lines.
Figure 2B:
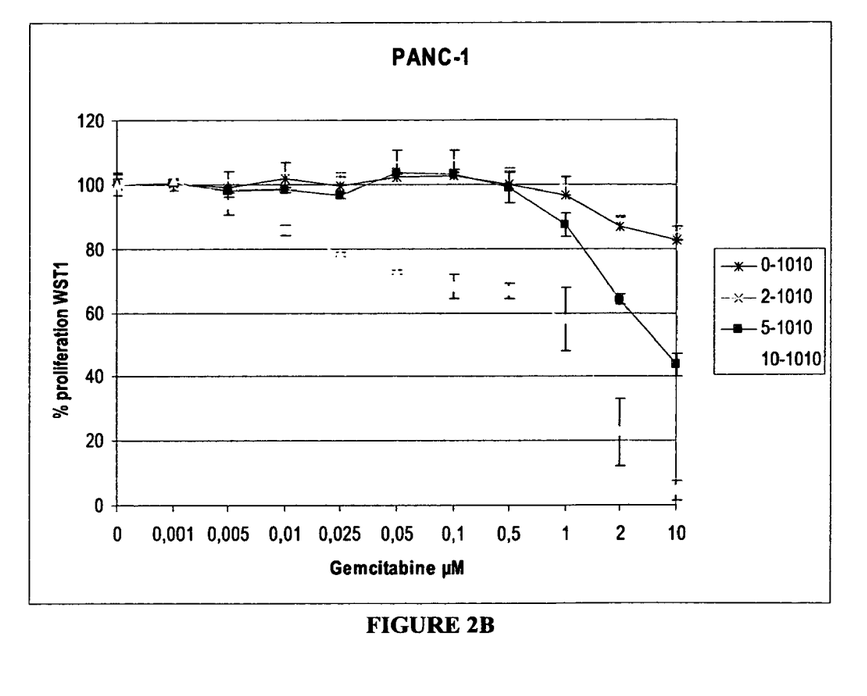

FIG. 2 clearly shows that AB1010 pretreatment (5 and 10 μM) reverse resistance of pancreatic tumour cell lines to gemcitabine while the sensitivity of the other cell lines remains unchanged (table 1).

TABLE 1

AB1010 sensitizes MiaPaca-2 and Panc-1 to gemcitabine

|  |  |  | AB1010 + Gemcitabine | |  |
| --- | --- | --- | --- | --- | --- |
| IC50 µM | AB1010 | Gemcitabine µM | AB1010 5 µM | AB1010 10 µM | Sensitization factor |
| MiaPaca-2 | 10 | >10 | 1.5 | 0.025 | 400 |
| Panc-1 | >10 | >10 | 8 | 1 | 10 |
| BxPC-3 | >10 | 0.1-1 | 0.1-1 | 0.1-1 | 0 |
| Capan-2 | 2 | 0.1-1 | 0.5-1 | ND | 0 |

The sensitization effect of AB1010 is not observed on gemcitabine-sensitive Capan-2 and BxPC-3 cell lines probably due to the strong anti-proliferative effect of gemcitabine on these cell lines. In addition, the sequence of drug treatment is important since pre-treating cells first with gemcitabine before exposing them to AB1010, does not result in a decrease of the IC50 of gemcitabine. This observation suggests that pre-treatment with AB1010 may alter the cells in a way that renders them more susceptible to further treatment with gemcitabine.

3.2 AB1010 Sensitizes Various Cancer Cell Types to Gemcitabine

In order to evaluate the ability of AB1010 to sensitize other tumour types to gemcitabine, we performed similar studies on prostate, lung, ovarian and colon tumour cell lines. The results of these studies are summarized in the Tables below.

TABLE 2

AB1010 sensitizes prostate DU145, and C4-2 cell lines to gemcitabine

| IC50 µM Cell lines | AB1010 µM | Gemcitabine µM | Gemcitabine + AB1010 | Sensitization factor |
| --- | --- | --- | --- | --- |
| DU145 | >20 | 100 | 10 | 10 |
| C4-2 | 15 | 20 | 1 | 20 |
| LnCAP | 15 | 10 | 5-10 | 0 |
| PC-3 | 8 | 10 | 10 | 0 |

TABLE 3

AB1010 sensitizes lung A549 and H1299 cell lines to gemcitabine

| IC50 µM Cell lines | AB1010 µM | Gemcitabine µM | Gemcitabine + AB1010 | Sensitization factor |
| --- | --- | --- | --- | --- |
| A549 | 8 | >100 | 10 | 10 |
| H1299 | 10 | >100 | 10-50 | 2 to 10 |
| H1650 | 7.5 | 1-5 | 5 | 0 |
| H1975 | 9 | 1-5 | 5 | 0 |

TABLE 4

AB1010 sensitizes rectum HRT-18, and colon Caco-2 and SW-480 cell lines to gemcitabine

| IC50 µM Cell lines | AB1010 µM | Gemcitabine µM | Gemcitabine + AB1010 | Sensitization factor |
| --- | --- | --- | --- | --- |
| Caco-2 | 7.5 | >100 | 25-50 | 2 to 4 |
| HRT-18 | >10 | >100 | 5-10 | 10 to 20 |
| SW-480 | 5 | 20 | 5-10 | 2 to 4 |
| HT-29 | 5 | >100 | >100 | 0 |
| LS-174T | 7.8 | 5-10 | 5-10 | 0 |

TABLE 5

AB1010 sensitizes ovarian OVCAR-3 cell lines to gemcitabine

| IC50 µM Cell lines | AB1010 µM | Gemcitabine µM | Gemcitabine + AB1010 | Sensitization factor |
| --- | --- | --- | --- | --- |
| OVCAR-3 | 10 | 50 | 10-20 | 2.5 to 5 |
| O170 | 7.5 | 1 | 1 | 0 |
| OV90 | 7.5 | 5-10 | 5-10 | 0 |
| TOV-112D | 7.5 | 5 | 5 | 0 |
| TOV-21G | 10 | 10 | 10 | 0 |

Figure 3A:
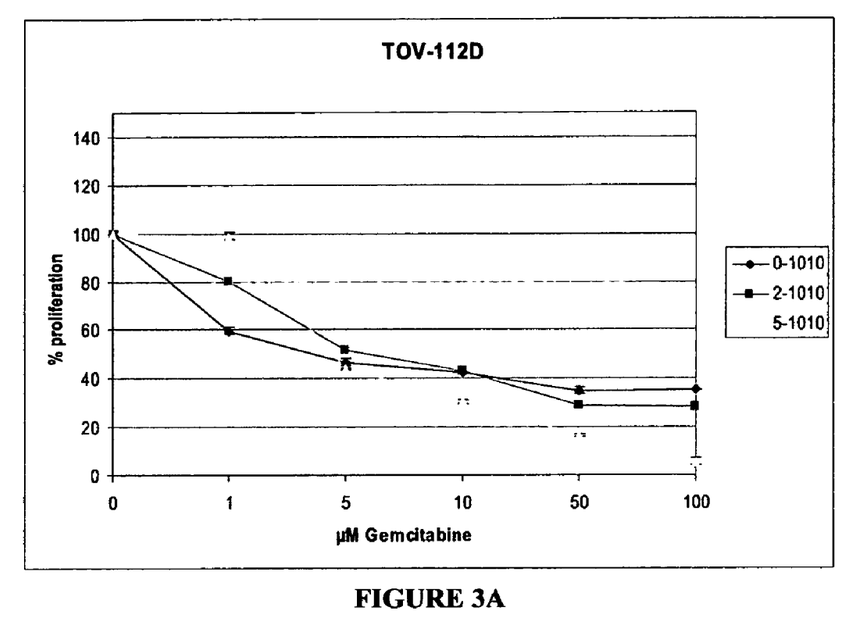
FIGS. 3A and 3B show the ability of AB1010 to partially block FAK activity.

We found that AB1010 restores to various degrees the sensitivity to gemcitabine of all resistant cancer cell lines except one (colon HT-29), including prostate (table 2), non-small cell lung (table 3) colorectal (table 4) and ovarian cell lines (table 5). When cells exhibit sensitivity to gemcitabine, AB1010 does not lower the 1050 of gemcitabine even though it might still potentiate the cytotoxic effect of gemcitabine by inducing close to 100% inhibition at lower dose of gemcitabine compare to gemcitabine alone (FIG. 3).

3.3 AB1010 Sensitizes Cancer Cell Lines to Standard Chemotherapies 3.3.1 AB1010 Sensitizes Breast and Ovarian Tumour Cell Lines to Taxanes We next tested the ability of AB1010 to sensitize ovarian and breast tumour cell lines to the action of anti-mitotic agents docetaxel or paclitaxel (chemotherapies of reference for the pathologies). Summary of the results is shown in Table 6 and 7.

TABLE 6

AB1010 sensitizes breast tumour cell lines to docetaxel

| IC50 μM Cell lines | AB1010 μM | Docetaxel μM | Docetaxel + AB1010 (10 μM) | Sensitization factor |
|---|---|---|---|---|
| SUM185 | 6.5 | >10 | 0.05 | 200 |
| HCC1937 | 7.5 | >10 | 1 | 10 |
| BT483 | 8 | >10 | 1 | 10 |
| MDAMB134 | >10 | >10 | 0.01 | 1000 |
| BT474 | 4 | 10 | 0.5 | 20 |
| SB8 | 6.5 | >1 | 0.06 | 20 |
| SUM190 | 10 | >10 | >10 | 0 |
| MCF-7 | >10 | >1 | 5 | 0 |
| A431 | 6.5 | 10 | 10 | 0 |
| HCC1500 | 9 | 10 | 10 | 0 |
| 184BS | >10 | 10 | 10 | 0 |
| BRCAMZ-01 | >10 | 0.02 | 0.03 | 0 |

Surprisingly most of the breast cancer cell lines tested exhibit resistance to Docetaxel.

We observe a good sensitization by AB1010 for 6 out of 11 of these resistant cell lines.

TABLE 7

AB1010 sensitize resistant ovarian tumour cell lines to Paclitaxel

| IC50 μM Cell lines | AB1010 μM | Paclitaxel μM | Paclitaxel + AB1010 | Sensitization factor |
|---|---|---|---|---|
| OV90 | 7.5 | >10 | 7.5 | 1.5 |
| OVCAR3 | 10 | >10 | 0.1 plateau | 100 |
| O170 | 7.5 | <0.1 | <0.1 | 0 |
| TOV112D | 7.5 | <0.1 | <0.1 | 0 |
| TOV21G | 10 | 0.1 | 0.1 | 0 |

Three out of the five ovarian cell lines tested exhibit strong sensitivity to the standard chemotherapeutic agent Paclitaxel. Interestingly AB1010 restores sensitivity to Paclitaxel of resistant tumor cell lines.

3.3.2 AB1010 Sensitizes Colon Tumour Cell Lines to Irinotecan (CPT-11)

We next tested the ability of AB1010 to sensitize resistant colorectal tumour cell lines to the action of anti-topoisomerase I Irinotecan (CPT-11) (chemotherapy of reference for the pathologies). Summary of the results is shown in Table 8.

TABLE 8

AB1010 sensitizes colon and rectum cell lines to Irinotecan

| IC50 μM Cell lines | AB1010 μM | Irinotecan μM | Irinotecan + AB1010 | Sensitization factor |
|---|---|---|---|---|
| HRT-18 | >10 | >100 | 30 | 3 |
| SW-480 | 5 | 40 | 15 | 2.5 |
| HT-29 | 5 | 50 | 50 | 0 |
| Caco-2 | 7.5 | 65 | 50 | 0 |
| LS-174T | 7.8 | 20 | 20 | 0 |

We observe a good sensitization by AB1010 for the most resistant cell lines HRT-18.

3.4 AB1010 but not STI571 Sensitizes Pancreas Mia Paca-2 Cancer Cell Lines to Gemcitabine The same type of experiments as previously described was performed comparing AB1010 and STI-571 pretreatment on the response of MiaPaca-2 tumour cell line to gemcitabine.

Figure 4:
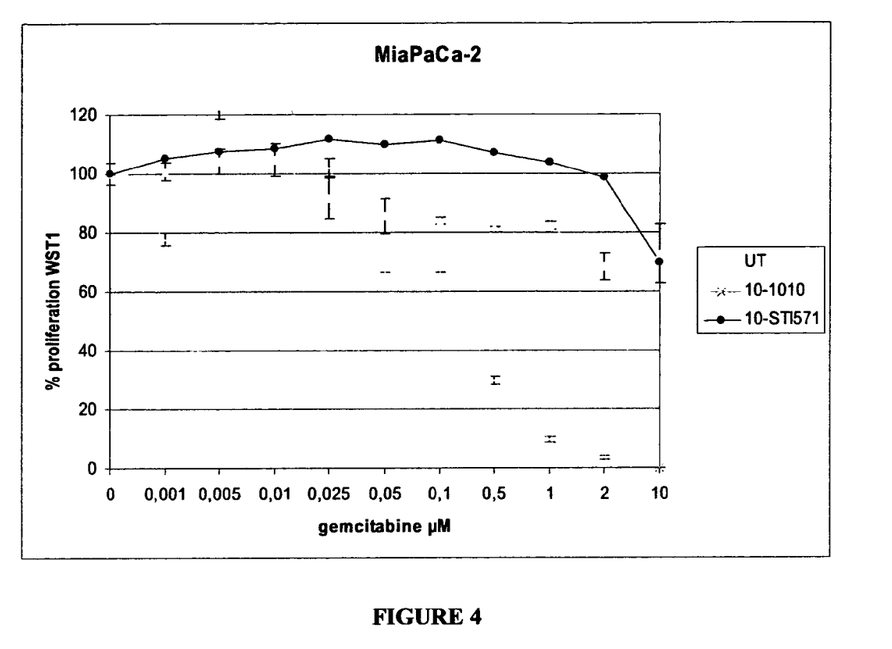
FIG. 4 shows that pre-treating cells with STI571 does not sensitize MiaPaca-2 to gemcitabine.
Figure 5:
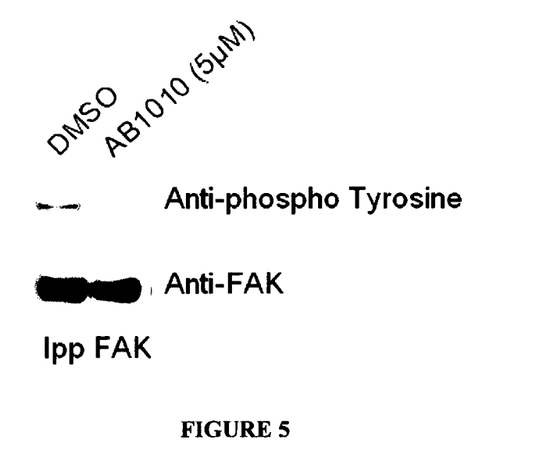
FIG. 5 shows the effect of AB1010 on FAK kinase.

As shown in FIG. 4, pre-treating cells with STI571 does not sensitize MiaPaca-2 to gemcitabine. Table 9 summarizes the IC50 of the drugs used individually or in combination on MiaPaca-2 cell line.

TABLE 9

Comparing AB1010 and STI571 on sensitizing MiaPaca-2 to gemcitabine (Gem)

| IC50 μM | Gem | STI571 10 μM | Gem + STI571 10 μM | AB1010 10 μM | Gem+ 1010 5 μM | Gem+ 1010 10 μM |
|---|---|---|---|---|---|---|
| MiaPaca-2 | >10 | >10 | >10 | 7 | 1.5 | 0.2 |

Sensitization effect to gemcitabine seems to be specific to AB1010 since pre-treatment with STI571 does not lead to the same result (even at 10 μM).

3.5 AB1010 may Sensitize Cancer Cell Lines Through Inhibition of the SRC-FAK Signalling Pathway In order to identify the targets of AB1010 in this process, we analysed the expression of RTK by RT-PCR in the pancreatic cell lines (data not shown). We found no detectable amount of c-Kit, suggesting that c-Kit might not be the main target. PDGFRβ was expressed in BxPC3, MiaPaca-2 and to a lower extent in Panc-1 while EGFR was highly expressed in all cell lines (data not shown). Therefore, there is no clear correlation between expression of the main targets of AB1010 and the response to the combination treatment of AB1010+ Gemcitabine.

Figure 3B:
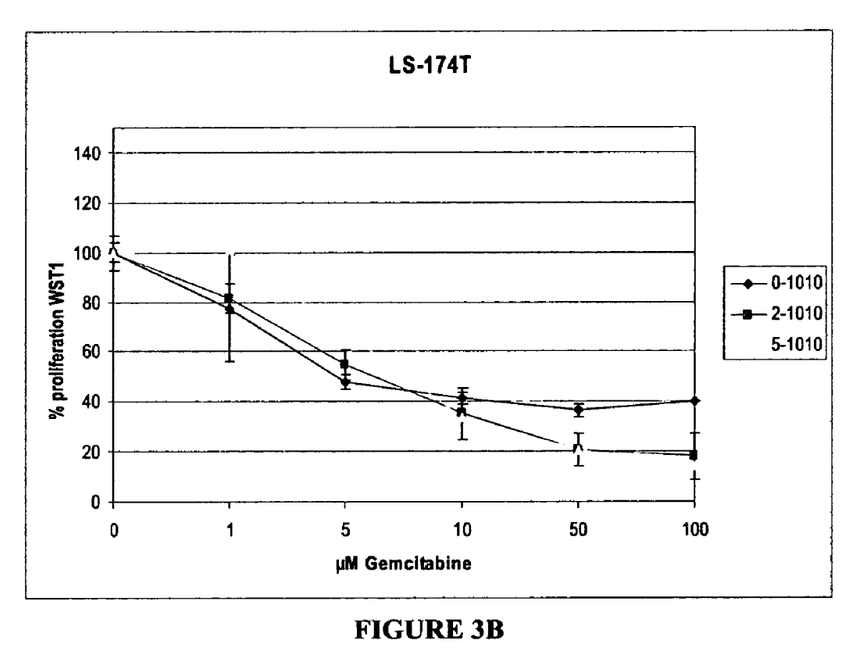

Pancreatic tumour cells lines are described to express high level of the non-receptor tyrosine kinase FAK that contributes to resistance to gemcitabine. Indeed, blocking FAK expression using siRNA has been shown to potentiate gemcitabine-induced cytotoxicity in vitro and in vivo (Duxbury et al. 2003, 2004). We now have preliminary data demonstrating that AB1010 is able to partially block FAK activity (FIG. 3). These data are supported by results obtained in a SelectScreen kinase Profiling of AB1010 performed for us by the Invitrogen Company. In this screen, the inhibitory activity of AB1010 used at 1 μM was tested on a panel of 205 purified kinases, showing 21% inhibition of FAK kinase activity. By the use of either anti PY or anti phospho FAK antibodies, we studied by western blot assay the activation status of FAK kinase. We confirmed that AB1010 inhibits partially FAK autoactivation (FIG. 3B). These data suggest the AB1010 may sensitize pancreatic tumour cell lines to gemcitabine through its inhibition of FAK kinase.

Since elevated FAK expression has been reported in other tumour types including prostate, colon and ovarian cancer, we propose a general mechanism of AB1010-sensitisation to cytotoxic agent through inhibition of FAK.

| Kinase Inhibitor | Gleevec ® (1,000 nM) | PP2 (1,000 nM) | AB1010 (1,000 nM) |
|---|---|---|---|
| Percentage of inhibition | 9% | 75% | 21% |

2.4—Discussion

This study is the first report showing in vitro that a selective inhibitor of c-Kit/PDGFRα&β, AB1010 is able to restore the sensitivity of resistant pancreatic tumor cell lines to the cytotoxic agent gemcitabine. The systematic sensitization of resistant cancer cell lines to gemcitabine by AB1010 is quite striking. Furthermore, sensitization to standard chemotherapies such as taxanes for Breast and Ovarian cancer cell lines and the anti-topoisomerase I Irinotecan for Colorectal cancer cell lines has been observed even though the synergistic effects were not as strong. Based on our data on FAK kinase, we think that AB1010 may sensitize cell lines partially by blocking the FAK-SRC signalling pathway leading to loss of adhesion properties as we were able to observe in our experiment.

We are aware that this study has been performed on a limited number of cell lines that do not necessarily reflect the complexity of tumour in vivo. Nevertheless the in vivo results of an ongoing phase II clinical trials conducted on patients with pancreatic cancer receiving a combination of AB1010+ gemcitabine seem to validate this approach.

Together our in vitro and in vivo results suggest that AB1010 has great potential in combination therapy with gemcitabine as well as with standard chemotherapies for the treatment of cancers such as pancreas, prostate, non-small cell lung cancer, breast and ovarian cancers. AB1010 might be particularly potent in cases of cancers relapsing after a first line of treatment and which are usually considered as chemoresistant tumours.

The invention claimed is:

1. A method for treating solid cancers resistant to a neoplastic agent comprising administering 4-(4-Methyl-piperazin-1-ylmethyl)-N-[4-methyl-3-(4-pyridin-3-yl-thiazol-2-ylamino)-phenytl]-benzamide (Masitinib-AB1010) and at least one antineoplastic agent in patients in need of such treatment.

2. The method according to claim 1 for the treatment of non-small cell lung cancer, pancreatic cancer, bladder cancer, breast cancer, ovarian cancer, prostate cancer, oesophageal cancer, colorectal cancer, and advanced biliary tract cancers.

3. The method according to one of claims 1 to 2, wherein said antineoplastic agent is selected from a marketed medicament for the treatment of cancers.

4. The method according to claim 3, wherein said antineoplastic agent is selected from antimitotics.

5. The method according to claim 4, wherein said antineoplastic agent is docetaxel.

6. The method according to claim 3, wherein said antineoplastic agent is selected from antimetabolites.

7. The method according to claim 6, wherein said antineoplastic agent is gemcitabine.

8. The method according to claim 3, wherein said antineoplastic agent is selected from anti-topoisomerase I.

9. The method according to claim 6, wherein the antimetabolite is a nucleotide analog.

10. The method according to claim 6, wherein the antimetabolite is chosen from purine analogs, pyrimidine analogs and adenine analogs.

11. The method according to claim 10, wherein the purine analog is chosen from thio-6-guanine and pentostatine; the pyrimidine analog is chosen from cytosine arabinoside, fluoro-5-uracile (5FU), fluorouridine-desoxyribose, capecitabine and gemcitabine; and the adenine analog is fludarabine.

12. The method according to claim 1, wherein masitinib and the antineoplastic agent are administered simultaneously, separately or sequentially.

13. The method according to claim 12 intended for the treatment of patients afflicted with unresectable pancreatic adenocarcinoma.

14. The method according to claim 13, wherein unresectable pancreatic adenocarcinoma is resistant to gemcitabine alone plus radiotherapy protocols.

15. The method according to claim 3, wherein said antineoplastic agent is a platinum analog.

16. The method according to claim 15, wherein said platinum analog is selected from cisplatin and carboplatin.

17. The method according to claim 3, wherein said antineoplastic agent is selected from lomustine and dacarbazine.

* * * * *